(12) United States Patent
Burke

(10) Patent No.: US 8,637,304 B1
(45) Date of Patent: Jan. 28, 2014

(54) AMMONIA NITROGEN RECOVERY THROUGH A BIOLOGICAL PROCESS

(76) Inventor: Dennis A. Burke, Olympia, WA (US)

( * ) Notice: Subject to any disclaimer, the term of this patent is extended or adjusted under 35 U.S.C. 154(b) by 16 days.

(21) Appl. No.: 13/373,860

(22) Filed: Dec. 1, 2011

Related U.S. Application Data

(60) Provisional application No. 61/516,050, filed on Mar. 29, 2011, provisional application No. 61/458,794, filed on Dec. 2, 2010, provisional application No. 61/458,938, filed on Dec. 6, 2010, provisional application No. 61/460,219, filed on Dec. 29, 2010.

(51) Int. Cl.
*C12P 1/00* (2006.01)
*C12P 5/00* (2006.01)
*C12M 1/34* (2006.01)
*C12M 3/00* (2006.01)
*C12M 1/02* (2006.01)

(52) U.S. Cl.
USPC ..... 435/290.1; 435/41; 435/288.4; 435/289.1

(58) Field of Classification Search
None
See application file for complete search history.

(56) References Cited

U.S. PATENT DOCUMENTS

| | | | |
|---|---|---|---|
| 4,710,300 A | 12/1987 | Kristoufek | |
| 5,384,404 A * | 1/1995 | Lee | 544/201 |
| 5,482,720 A * | 1/1996 | Murphy et al. | 424/489 |
| 5,529,692 A | 6/1996 | Kubler | |
| 6,113,786 A | 9/2000 | Burke | |
| 6,464,875 B1 | 10/2002 | Woodruff | |
| 6,500,340 B1 | 12/2002 | Burke | |
| 6,521,129 B1 | 2/2003 | Stamper et al. | |
| 6,866,779 B1 | 3/2005 | Burke | |
| 7,153,427 B2 | 12/2006 | Burke | |
| 7,160,456 B2 | 1/2007 | Jarventie | |
| 7,811,455 B2 | 10/2010 | Burke | |
| 2008/0302722 A1* | 12/2008 | Burke | 210/603 |
| 2009/0203067 A1* | 8/2009 | Eckerle et al. | 435/41 |

* cited by examiner

*Primary Examiner* — Thane Underdahl
(74) *Attorney, Agent, or Firm* — Brian J. Coyne

(57) ABSTRACT

An economical method for recovering nitrogen from liquid waste using autotrophic organisms and minimal energy inputs and without chemical additives. Solids are separated from anaerobically digested liquid waste. The resulting translucent liquid is introduced to a culture of autotrophic microorganisms in the presence of natural or artificial light, thereby accumulating biomass and producing a liquid effluent with elevated pH. The elevated-pH, liquid effluent is heated and stripped of ammonia, thereby producing a water vapor and stripped ammonia gas stream. The water vapor ammonia gas stream is condensed to form a liquid/ammonia condensate. The autotrophic microorganisms are advantageously cultivated in a photobioreactor comprising a plurality of axially spaced-apart, growth plates mounted for rotation to a shaft. The pH of the culture is adjustable within a preferred range of 8.0 to 10.5 by adjusting the light intensity and rotational speed.

41 Claims, 10 Drawing Sheets

EXAMPLE OF STRIPPING UNIT WITH
SEPARATE WATER VAPOR REMOVAL

AMMONIA NITROGEN RECOVERY THROUGH A BIOLOGICAL PROCESS

CROSS REFERENCE TO RELATED APPLICATIONS

This application claims the benefit of the following provisional applications by the same applicant for the same invention, the disclosures of which are incorporated herein, filed on:

Mar. 29, 2011, application No. 61/516,050, entitled, "Control of Water Vapor from High Temperature Stripping;"

Dec. 2, 2010, application No. 61/458,794, entitled, "Ammonia Condensate Recovery Process;"

Dec. 6, 2010, application No. 61/458,938, entitled, "Ammonia Nitrogen Recovery through Natural Biological Process;" and Dec. 29, 2010, application No. 61/460,219, entitled, "Apparatus and Process for Growing Autotrophic Organisms."

STATEMENT REGARDING GOVERNMENT RESEARCH

The U.S. Department of Agriculture funded proof of concept research under U.S. Department of Agriculture 2010 SBIR project number 2010-33610-20920.

BACKGROUND OF THE INVENTION

1. Field of Invention

This invention is an economical method of recovering nitrogen as a product from biomass through the use of autotrophic organisms without the use of chemicals and with minimal energy inputs. The same process will convert low BTU biogas to high BTU biomethane gas.

2. Background Art

To control greenhouse gas induced global warming, methane gas emissions to the atmosphere from decomposition of waste residuals, such as food waste and animal manure, have been discouraged. However, anaerobic digestion (AD) is not a particularly economical process. The economics can be improved by: (1) exporting the energy as higher valued biomethane transportation fuel rather than electricity, and (2) co-digesting other waste residuals and thereby obtain a tipping fee—i.e., a fee charged to deliver municipal waste to a landfill, waste-to-energy facility or recycling facility. The first option is not particularly advantageous since the physical/chemical processes available to upgrade biogas to biomethane are expensive and have a cost approximately equal to the value of the natural gas or the biomethane produced. The second option, the co-digestion of additional substrates, increases protein conversion to ammonia and fugitive emissions of ammonia nitrogen to the atmosphere resulting in the creation of fine particulate matter ($PM_{2.5}$), as well as biogenic $NO_x$, $N_2O$, and ozone. $N_2O$ is a powerful greenhouse gas at 310 times $CO_2$ and the primary chemical responsible for stratospheric ozone depletion. Consequently, the discharge of ammonia nitrogen from anaerobic decomposition of organic and co-digested substrates results in significant adverse environmental and public health impacts.

Ammonia discharges from anaerobic digestion are strictly controlled in the EU and are expected to be controlled throughout the US. A number of technologies have been developed over the years to remove ammonia nitrogen from liquid waste streams through a variety of physical, chemical and biological methods. All of these processes are energy intensive, and expensive. Consequently, there is little incentive to curtail well-known and documented ammonia emissions from anaerobic digestion. It is expected that current and future regulation of ammonia nitrogen emissions will constitute a barrier to future implementation of renewable energy anaerobic digestion technologies.

All organic material contains 5% to 15% nitrogen (Redfield ratio, C:106, N:16, P:1). Digestion of high solid concentration, nitrogen rich, substrates such as food waste, algae, crop residues, whole ethanol stillage, poultry manure, etc. is hindered by ammonia toxicity created through the decomposition of protein. Ammonia toxicities to anaerobic microbes occur at concentrations exceeding 1,500 mg per liter, which will occur when the substrate solids concentrations exceed 6% solids, that contain 5% or more of nitrogen, and when the solids conversion to methane gas (bioconversion) exceeds 50%. Most high solids substrates such as poultry manure, food waste, and crop residues have solids concentrations exceeding 6% and nitrogen concentrations exceeding 5%. It is also desirable to convert more than 50% of the solids to gas and thereby maximize gas production. For poultry manure, dilution of the solids concentration from 40% to values as low as 6% solids requires substantial quantities of water that must be disposed after liquid solids separation. Such dilutions are typically not feasible. To overcome the dilution obstacle, a number of EU technologies such as the DRANCO, Valorga, and Kompogas have been developed to recycle the digestate liquid to the liquids/separation_step and thereby reduce the quantity of dilution water necessary to achieve lower solids concentrations. However, ammonia toxicity remains when the recycled digestate contains excessive ammonia, i.e. the ammonia is not removed.

In summary, the removal and reclamation of ammonia is important to improve the anaerobic digestion of organic residuals and minimize adverse environmental and public health impacts. The economical reclamation of ammonia as well as the production of high BTU gas will significantly improve the economics of AD.

3. Description of Related Art

Many strategies have been developed to remove and sequester ammonia nitrogen from the effluent of an anaerobic reactor. The basic strategy is to remove the ammonia from solution and form a second liquid or solid ammonium compound. Removing the ammonia from the digester effluent is normally preceded by decarbonization to remove $CO_2$, followed by the addition of a chemical reagent, such as calcium, sodium or magnesium hydroxide to raise the solution pH and thereby shift the ionized ammonium to the unionized ammonia gas form (U.S. Pat. No. 4,104,131). Air containing a low concentration of ammonia is then used to strip the ammonia gas from solution. Steam has also been used to raise temperature, reduce the solubility of carbon dioxide, increase the pH, and strip ammonia gas from solution by reducing the pressure and thereby decreasing the partial pressure of $CO_2$ (U.S. Pat. No. 6,521,129).

High temperature (60-70.degree.C.) reduced pressure (0.25-0.75 bar) stripping has also been proposed (U.S. Pat. No. 6,368,849 B1). High temperature distillation or rectification of carbon dioxide and ammonia at an elevated temperature has been proposed (U.S. Pat. Nos. 4,710,300 and 6,368, 849 B1). Membrane processes with decarbonization and pH adjustment have likewise been proposed. Pressurizing the digester contents and driving $CO_2$ into solution has also been practiced. All these processes require a significant investment in energy for heat and pressure, and reagents for pH adjustment. Scale formation is a common problem if calcium or magnesium is used to adjust pH. Rectification or high temperature stripping requires the removal of most suspended solids prior to high temperature steam stripping or rectification.

Following ammonia stripping the ammonia can be sequestered through a variety of means. If high-temperature distillation is used to remove both carbon dioxide and ammonia, the uncontrolled formation of ammonium bicarbonate solids (scale) can be mechanically removed from the stripping unit (U.S. Pat. No. 4,710,300). If the ammonia is stripped with air or steam, anhydrous ammonia or aqueous ammonia can be formed at a reduced pH (U.S. Pat. No. 6,464,875, U.S. Pat. No. 5,702,572). If ammonia is stripped with air or steam ammonium salts can be formed through a reaction with a dilute acid (U.S. Pat. No. 6,521,129).

Biological processes have been used to remove ammonia nitrogen. They include aerobic nitrification and denitrification and the Anammox process whereby ammonia is anaerobically converted to nitrogen gas resulting in the loss of ammonia nitrogen's fertilizer value.

High temperature reduced pressure stripping, as well as distillation to remove both carbon dioxide and ammonia will improve the biogas quality since a portion of the carbon dioxide is removed from the gas stream under the high temperature conditions (U.S. Pat. No. 4,710,300). Improved gas quality has also been claimed when digesting a substrate having a high concentration of nitrogen through the formation of ammonium bicarbonate in solution (U.S. Pat. No. 7,160,456 B2). Also, biogas quality improvements have been claimed for processes that pass biogas through the digester liquid containing ammonia to form ammonium carbonate in the liquid slurry (U.S. Pat. No. 4,372,856, and U.S. Pat. No. 7,160,456).

A variety of processes are utilized to directly improve the BTU content of biogas. These processes involve the removal of carbon dioxide by high-pressure water scrubbing (U.S. Pat. No. 6,299,774), amine scrubbing, and membrane separation. Most of the systems involved high-pressure operation with significant capital and operation and maintenance costs. Biological processes have also been used such as acid phase anaerobic digestion (U.S. Pat. No. 5,529,692) where the $CO_2$, formed in the acid phase, is separately removed from the predominately methane gas stream from the methane phase.

The economics of ammonia removal and sequestration, as well as the production of a high BTU biogas, can be improved significantly by operating a low pressure, low temperature, process that can remove substantially all of the ammonia while controlling the quality of the biogas produced. The process would be even more advantageous if it can be performed without the use of costly chemical reagents.

SUMMARY OF THE INVENTION

This invention can be visualized as a simple four step process. The first step of the process following anaerobic digestion is gas/solids separation for the removal of fine particulate matter and the stripping of $CO_2$ from the influent. The separation unit increases the pH from 7.5± to about 8.3± through the removal of $CO_2$ gas. The increased pH shifts the ammonia from the dissolved ammonium ion form to the ammonia gas form that can be stripped. The second step of the process uses autotrophic organisms to increase the pH from about 8.3± to 10.5±. Natural and/or artificial light and any of a variety of autotrophic organisms are used to consume the bicarbonate in solution to produce oxygen and raise the pH. The use of autotrophic organisms eliminates the need for costly chemicals and sludge disposal. The third step of the process is heating the liquid with recovered heat and stripping of ammonia gas from the liquid. The fourth step of the process is the precipitation of the stripped ammonia gas with the carbon dioxide from the anaerobic digester's biogas to produce an ammonium bicarbonate solid ($NH_3+H_2O+CO_2+CH_4 \rightarrow CH_4+NH_4HCO_3$) and biomethane or natural gas transportation fuel.

DETAILED DESCRIPTION OF THE INVENTION

Figure 1:
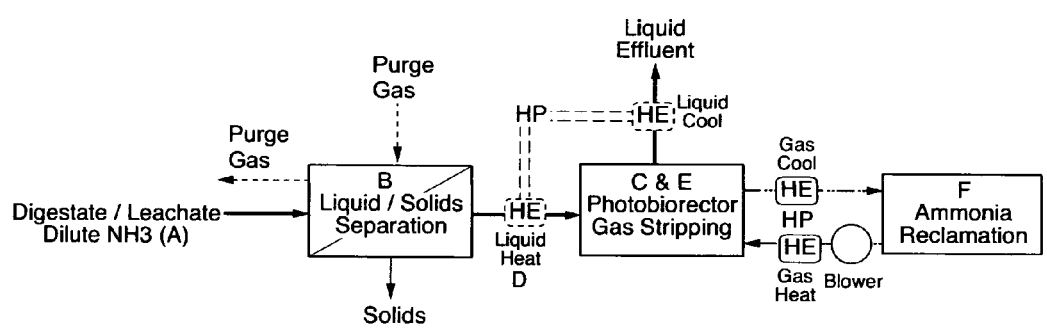
FIG. 1 presents the simplest version of the method of the invention for processing dilute solutions of ammonia. The simple, dashed lines represent optional configurations.

The essence of this invention is the elimination of chemicals commonly used for the stripping and recovery of nitrogen from anaerobically digested biomass. Typically, the chemicals are toxic, add cost, and produce a sludge. This invention uses $CO_2$ stripping and autotrophic organisms that consume bicarbonate to increase the pH of the digestate. The economics of the process is predicated on developing a substantial and rapidly growing biomass to consume the carbon dioxide and bicarbonate as quickly as possible.

The growth of autotrophic organisms requires suitable environmental conditions such as pH, temperature, and absence of toxic constituents. This invention proposes to increase the pH to levels that are inhibitory to autotroph growth while processing a highly toxic ammonia rich digestate solution that also inhibits growth. This invention overcomes those limitations by first stripping the ammonia from the digestate prior to processing the digestate through a photobioreactor. At the same time a purge gas is used to strip any ammonia gas generated from dissolved ammonium while the pH is increasing in the photobioreactor.

The growth of autotrophic organisms also requires sufficient light transmission to a concentrated solution of organisms. However, this invention proposes to process a turbid, colored, and autotrophic organism suspended solids rich solution. This invention overcomes those turbidity limitations by first removing the suspended solids from the digestate while using an attached growth photobioreactor that accumulates large concentrations of organisms without inhibiting light transmission to those organisms. The efficiency of pH adjustment, organism growth, and bicarbonate consumption can be controlled by light intensity, rotation speed, and carbon dioxide exposure to air.

Use of autotrophic organism limits the pH that can be achieved prior to stripping since the organism growth is inhibited above pH 10.5. As a result the temperature must also be increased to achieve high rates of ammonia removal at high temperatures and pH. However, increasing the temperature increases the water vapor and heat loss from the stripping unit. The increased loss of water vapor dilutes the stripped ammonia gas resulting in a lower valued product. This invention proposes to increase the concentration of the stripped product by re-stripping the product to produce a more concentrated product and/or to remove stripped water vapor through the use of a water vapor gas permeable membrane.

This invention also proposes to produce biomethane gas through the process. However, the autotrophic organisms will generate significant concentrations of oxygen that could contaminate the biogas or biomethane. In addition digestate processing that produces the ammonia supply may be intermittent while the biogas production is continuous throughout the day. In order to overcome the production and contamination issues this invention first produces a condensate that can be stored and used throughout the day to produce biomethane and ammonium bicarbonate.

Anaerobic digestion produces methane gas from the biomass COD and ammonia from the biomass nitrogen. However the ratio of COD to N concentrations vary considerably between the various biomass sources. As a result the quantity of methane and ammonia produced are variable. In most cases sufficient nitrogen is not available to precipitate all of the carbon dioxide and to produce a high purity biomethane gas. In addition increasing the pH of the digestate to strip the ammonia produces a high pH liquid effluent. This invention proposed to pretreat the biogas to remove a portion of the $CO_2$ with the high pH liquid effluent and thereby produce a lower $CO_2$ concentration gas for biomethane production while producing a higher pH effluent.

The simplest process configuration shown in FIG. 1, consists of the following steps: (a) anaerobically digesting the biomass or waste residuals in any of a variety of mesophilic or thermophilic anaerobic bioreactors. Anaerobic digestion produces a process gas stream containing primarily $CO_2$, methane, and water vapor, with trace concentrations of hydrogen sulfide and nitrogen, and a liquid stream fully saturated with $CO_2$ and methane gas, suspended solids, and a variety of dissolved organic and inorganic compounds including $NH_4+$; (b) liquid solids separation wherein the suspended solids are substantially removed to produce a translucent liquid capable of light transmission and containing primarily dissolved organic and inorganic constituents with dissolved gases; (c) increasing the pH of the translucent liquid through the use of a photobioreactor to remove $CO_2$ and bicarbonate and thereby increase the pH of the translucent liquid to values that convert a significant portion of the ionized ammonium ($NH_4+$) to ammonia gas ($NH_3$); (d) heating the high pH translucent liquid to improve stripping; (e) stripping the ammonia gas from the translucent heated liquid produced in "d" above, that has an elevated pH and temperature, with a stripping gas; (f) cooling the stripping gas produced in "e" above to produce a concentrate from which ammonia can be reclaimed as a product.

Any number of the steps (a through f) can be performed in a single or multiple reactors. For example the liquid solid separation step may consist of dewatering with any of a variety of conventional solids separators followed by gas stripping with a "purge gas" or use of a single reactor such as a gas flotation device that separates solids while stripping carbon dioxide, thereby increasing the pH and removing the suspended solids in the same reactor. Gas stripping may also occur in a single reactor composed of a photobioreactor incorporating gas stripping or a heated, gas stripping, photobioreactor.

Figure 2:
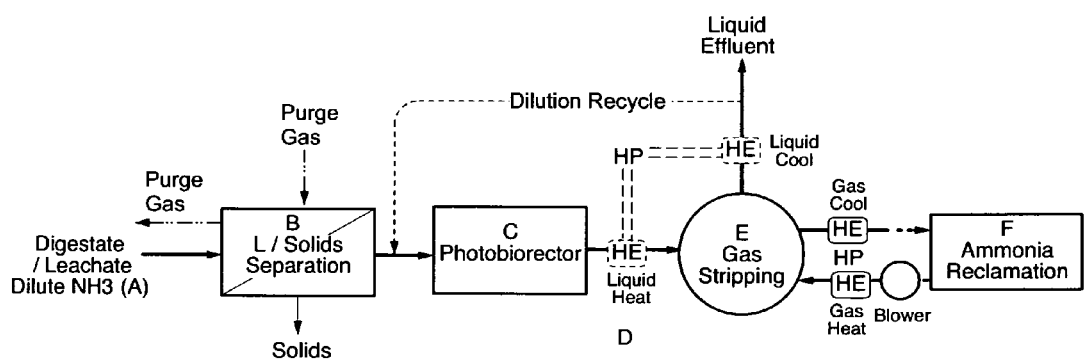
FIG. 2 presents a more complex version of the method of the invention for processing digestate or leachate having dilute concentrations of ammonia nitrogen.
Figure 4:
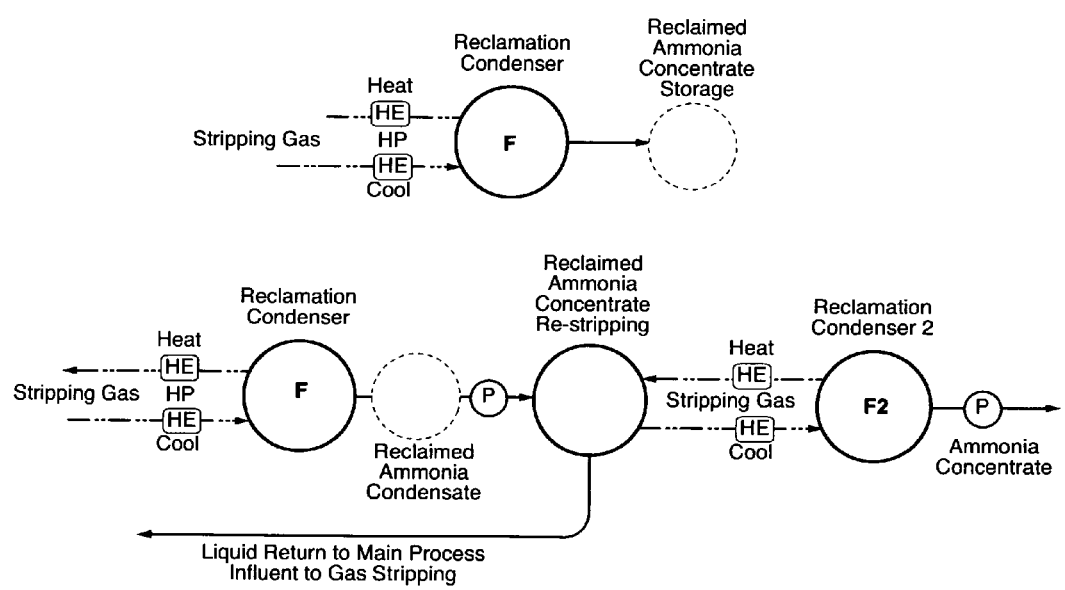
FIG. 4 presents alternative ammonia concentrate reclamation processes consisting of simple condensate reclamation and re-stripping reclamation.
Figure 5:
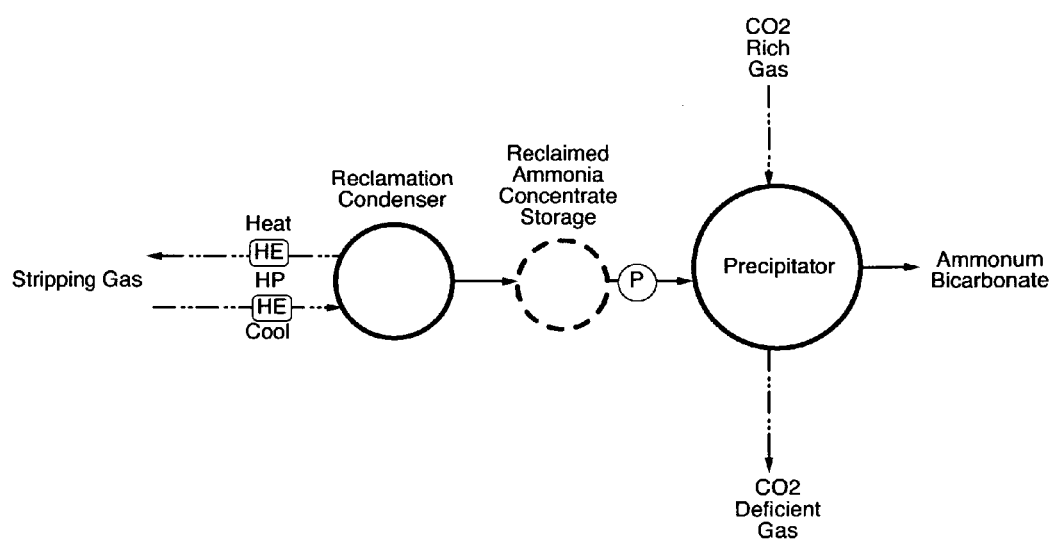
FIG. 5 presents a process for recovering ammonium bicarbonate while producing a $CO_2$-deficient gas. The dashed lines represent alternative configurations.

FIG. 2 presents an amplified version of FIG. 1. Anaerobic digestion (A) is followed by liquid/solids separation (B), which may use a purge gas such as air, to remove the dissolved $CO_2$ gas contained in the digestate at a low temperatures and pH, thereby inhibiting the loss of ammonia gas. Such a liquid/solids separation device is presented in FIG. 3. In FIG. 2, the liquid/solids separation (B) is followed by a photobioreactor (C) that further increases the pH by removing residual $CO_2$ and bicarbonate. The temperature of the photobioreactor is maintained at a value consistent with the growth culture that removes $CO_2$ and bicarbonate necessary to achieve the desired pH. The translucent liquid effluent can be heated following photobioreactor treatment to significantly higher values and thereby achieve greater conversion of ammonium ($NH_4+$) to ammonia ($NH_3$) gas to be stripped. After increasing the pH in the photobioreactor (C) effluent, and heating (D) the effluent to the desired values, the treated digestate is transferred to a liquid/gas stripping unit (E) that utilizes a gas stream to strip the ammonia gas from the liquid effluent. The stripping gas stream can be any warm gas, such as air that operates at suitable temperature and flow rates to achieve the desired ammonia gas removal from the liquid. The heated gas stream is delivered to the stripping unit under any desired pressure, temperature and flow rate established by a recirculating stripping gas blower. A separate gas heating unit may not be required if the blower produces sufficient gas temperatures. The stripping unit produces two effluent streams: a liquid from which the ammonia has been removed and a warm stripping gas stream enriched with water vapor and ammonia gas. Following stripping, the enriched stripping gas stream is cooled (HE) to produce a condensate or concentrate from which ammonia is reclaimed as a product (F). FIGS. 4 and 5 present optional ammonia reclamation arrangements. As shown in FIG. 2 the cooled stripping gas, deficient in ammonia gas and water vapor, is returned from the ammonia reclamation process (F) to the stripping unit after passing through an influent blower and a heat exchanger (HE) that provides the desired heat to the stripping gas.

The cooling of the stripping gas and heating of the gas returned from ammonia reclamation can be accomplished by a heat pump (HP) that cools the effluent stripping gas and heats the influent stripping gas. Heat provided to the liquid heat exchanger, influent to the stripping unit, can be recovered heat or waste heat from any of a variety of process sources including the hot liquid process effluent. As shown in FIG. 2, heat can be extracted from the liquid effluent (HE) and used to heat the stripping unit influent through a heat exchanger (HE) or the use of a heat pump (HP).

The processes presented in FIGS. 1 and 2 can be applied to digestate or landfill leachate that have dilute ammonia concentrations. Since ammonia nitrogen is toxic to most autotrophic organisms the influent can be diluted by recycling treated effluent or any liquid deficient in ammonia to produce a suitable influent photobioreactor stream.

Figure 3:
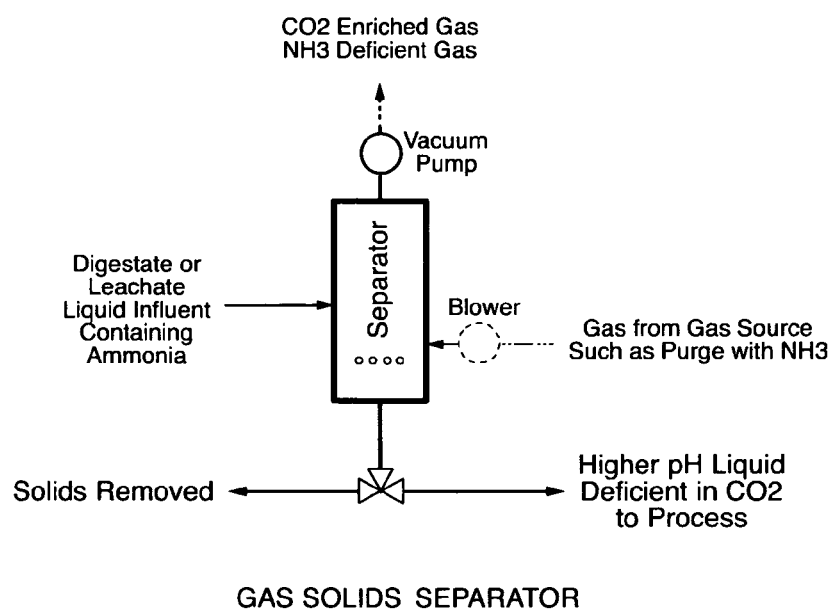
FIG. 3 presents a liquid, solids, and gas separator to be used to remove suspended solids and dissolved gases from the influent with dashed, light lines representing alternative configurations.

FIG. 3 presents a schematic of a $CO_2$ stripping liquid/solids separator that may use a gas blower to provide the required stripping gas or a vacuum pump that induces the liberation of flotation gases from the dissolved $CO_2$ and methane gas present in the digestate or leachate. Since sufficient dissolved gas may not be present to achieve the desired flotation gas/solids ratio for high solids concentration streams, the device can use additional pressurized or unpressurized gas from another source to induce flotation. The use of vacuum and induced gas is the preferred option. It is also beneficial to utilize purge gas from the photobioreactor as the induced gas since that gas is deficient in $CO_2$ and contains residual ammonia stripped from the photobioreactor. At normal operating low temperature and pH conditions, the ammonia present in the purge gas will be dissolved into the influent digestate liquid while the $CO_2$ gas is stripped, thereby increasing the pH. A $CO_2$ enriched and ammonia deficient effluent gas is produced while an ammonia enriched, $CO_2$-deficient, higher-pH liquid is produced through the liquid/solids separation process.

FIG. 4 presents alternative methods of recovering ammonia from the stripped gas/water vapor mixture. The stripped gas vapor mixture is cooled and condensed in condenser F. The condensate can subsequently be reclaimed and stored if necessary as a concentrated liquid ammonia product. The stripping gas is reheated preferably with a heat pump upon leaving the condenser. In the alternative, the condensate can be pumped to a second, third or fourth, etc. gas stripping unit where a second third or fourth more concentrated condensate is formed. The stripped liquid is then returned to the influent of the preceding stripping chamber. The reclaimed ammonia concentrate can be sold as an ammonia product or used to produce an ammonium bicarbonate solid product.

Figure 9:
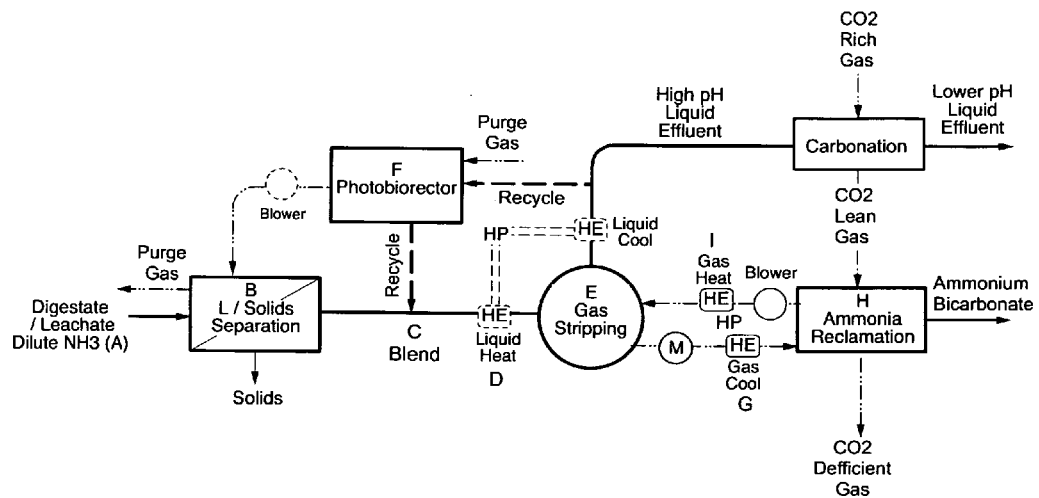
FIG. 9 presents an alternative, preferred embodiment of the invention, incorporating carbonation of the effluent while producing a lean $CO_2$ gas.

FIG. 5 presents a schematic where the stripped gas/water vapor mixture is condensed and reclaimed as a concentrate as described in FIG. 4 and stored as reclaimed concentrate for subsequent use in a gas liquid precipitator (F). The concentrate is pumped to the precipitator. The concentrate is then dispersed by spray nozzles or dispersion plates in the precipitator. A $CO_2$-rich gas, such as biogas, is then fed into the precipitator where it is contacted with the ammonia concentrate. An ammonium bicarbonate/carbonate solid is then formed ($NH_3+CO_2+H_2O \rightarrow NH_4HCO_3$), precipitated, and removed from the precipitator as a solid or semisolid product. Carbon dioxide is removed from the $CO_2$-enriched influent gas, such as digester biogas, to produce a gas product deficient in $CO_2$, such as natural gas or biomethane. The $CO_2$-enriched gas can also be a gas that has been pretreated to remove a portion of the $CO_2$ necessary to achieve the required stoichiometric ratios. FIG. 9 presents such a pretreatment schematic.

The concentrate can also be accumulated and stored during the production period when the solids are withdrawn from the digester. The stored concentrate can then be withdrawn on an intermittent or continuous basis to match the $CO_2$-enriched gas stream. The concentrate and gas flow rates can be controlled by monitoring effluent gas stream quality to produce a product gas of desired quality.

Figure 6:
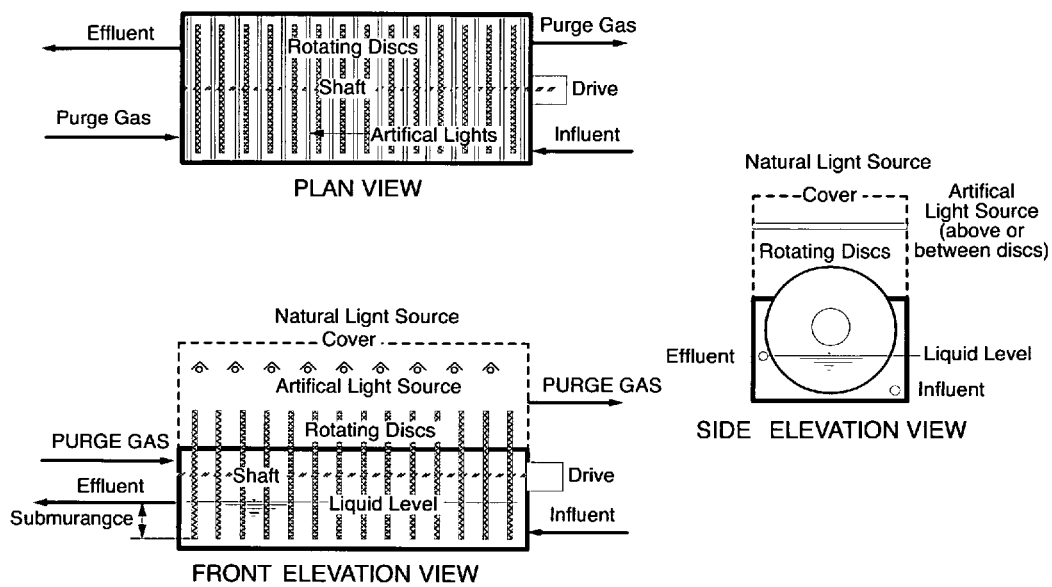
FIG. 6 presents plan and elevational views of a preferred embodiment of the autotrophic photobioreactor of the present invention.

FIG. 6 presents an improved photobioreactor for processing liquid and gas streams described earlier. Gas can be processed at low pressure since it is not dispersed in a liquid. Large biomass concentrations can be achieved due to the large surface area to volume ratio provided. Turbid liquids can be processed since hindrance of light penetration through a liquid to the microorganisms is minimized. In essence the process is not limited by gas transfer, light transmission, and biomass accumulation as typical, prior art photobioreactors are limited.

The device consists of a vessel containing a liquid substrate of variable depth, a series of rotating discs or media upon which autotrophic organisms are grown and illuminated by artificial or natural light. If artificial light is used, the ability to vary the intensity will provide a means for controlling growth and pH. The artificial light should be arranged to provide maximum illumination of the media surface. The discs rotate through the liquid substrate and the gas phase that is illuminated. The submergence depth can be varied to optimize the process. A shaft supports the discs and can be driven by air, gas or a motor. The speed of rotation can be varied to maximize performance. The vessel can be covered or open. If covered, a transparent cover should be provided for natural light. A blower that can move gas over the disc surface will provide a means of removing toxic gases and oxygen to minimize growth inhibition. Any of a variety of biomass removal devices can be used to harvest the autotrophic organisms grown to recover products. The product biomass may be returned to the digester and converted by anaerobic digestion to biogas, and the biogas can be used as an energy source. Light can be provided above or in between the rotating disks.

Figure 7:
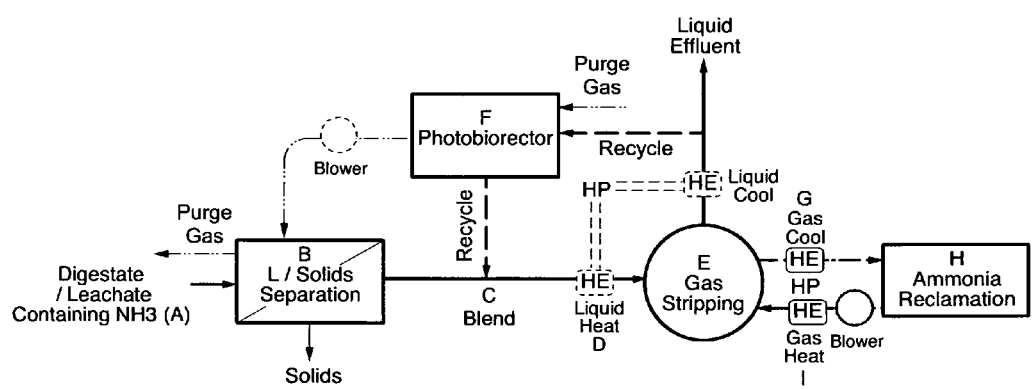
FIG. 7 presents a preferred embodiment of the invention for use on concentrated ammonia streams.

FIG. 7 presents a schematic for processing digestate containing higher concentrations of ammonia nitrogen. In most cases the growth of cyanobacteria and algae is inhibited by ammonia concentrations exceeding 30 mg/L. Consequently dewatered and degassed digestate containing higher concentrations of ammonia can not be efficiently processed in a photobioreactor to raise the pH. Although it may be possible to recycle treated effluent and thereby dilute the influent to the photobioreactor as shown in FIG. 2, such an arrangement will require substantially higher recycle rates, resulting in higher photobioreactor and stripping unit flow rates, size, and cost.

FIG. 7 presents an arrangement in which the photobioreactor (F) follows the gas stripping unit (E) rather than preceding the gas stripping unit. The high pH effluent from the photobioreactor (F) is blended at some recycle ratio to increase the pH of the liquid influent to the stripping unit (D). Ammonia gas is removed in the stripping unit with a portion of the effluent recycled to the photobioreactor. The arrangement shown in FIG. 7 dilutes the influent with a high pH recycle stream that both increases the pH and lowers the concentration of the influent to the stripping unit.

The stripping unit must produce an effluent low in ammonia and at a temperature suitable for the cultured photobioreactor organisms. A heat exchanger or heat exchangers (HE) with a heat pump (HP) are used to heat the influent to the stripping unit and cool the effluent.

A purge gas can be introduced into the photo bioreactor to remove oxygen and ammonia gas that may be present in the photobioreactor as a result of higher ammonia concentrations in the effluent. The purge gas is then introduced into a gas stripping liquid/solids separator (B) to reclaim any stripped ammonia. The gas stream used for stripping ammonia in the stripping unit (E) is first heated prior to stripping and cooled after stripping for ammonia reclamation.

Figure 8:
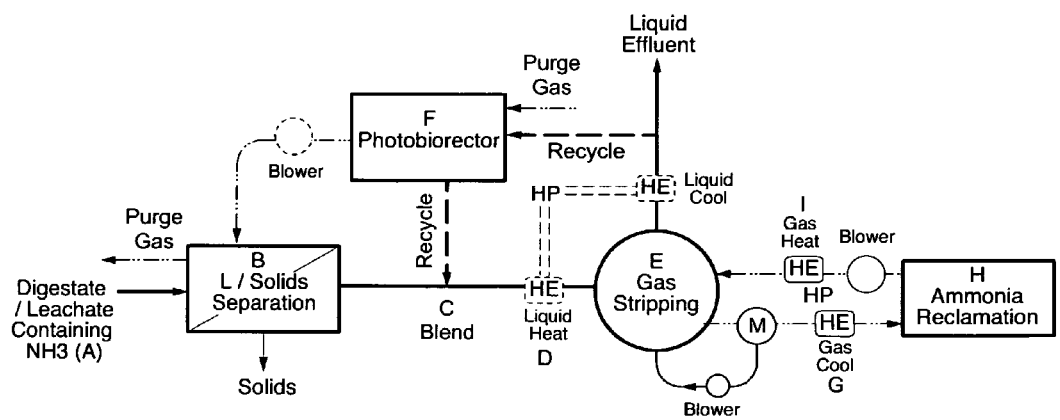
FIG. 8 presents an alternative, preferred embodiment of the invention incorporating a membrane gas separator for removing water vapor.
Figure 10:
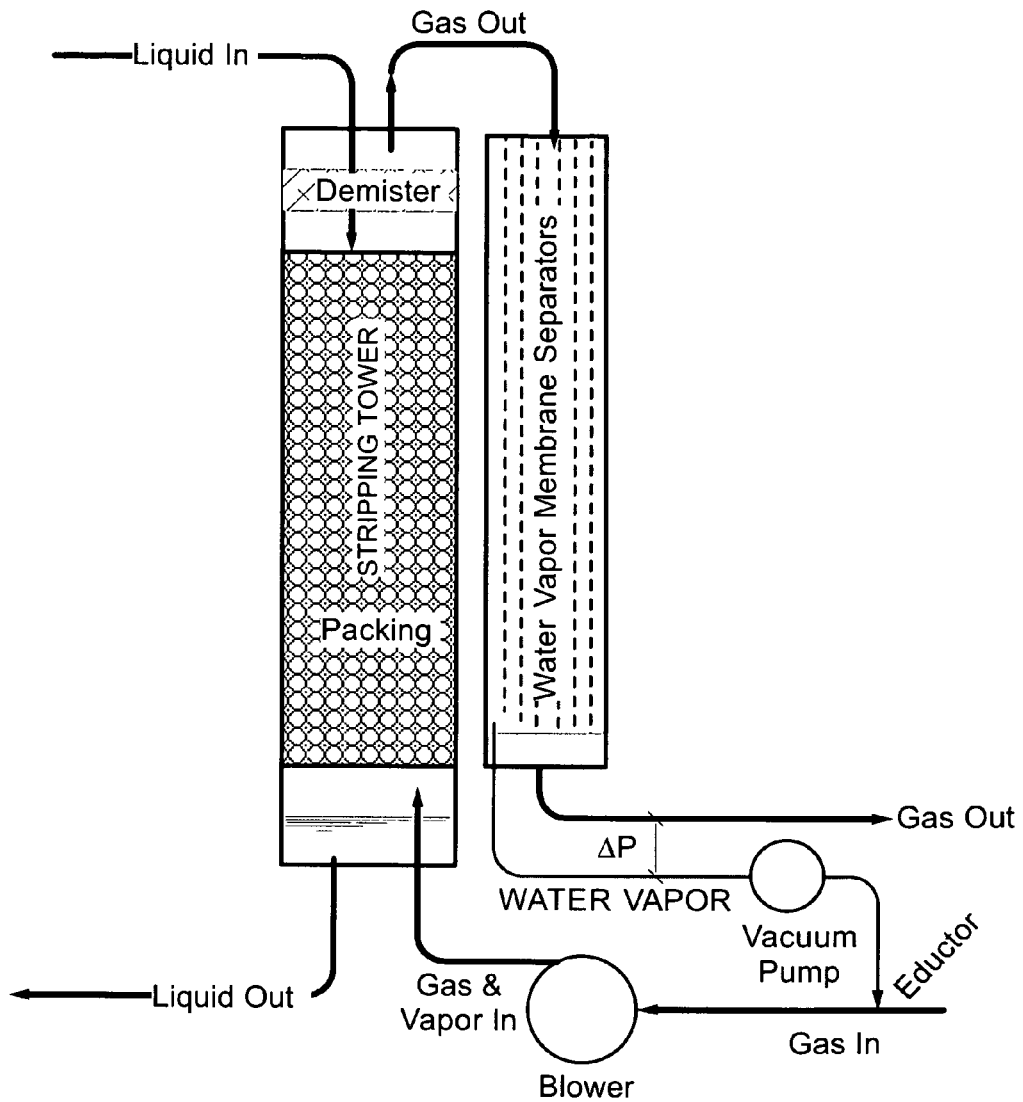
FIG. 10 presents an illustration, and an elevational view, of a process for removing water vapor from the stripping gas effluent.

FIG. 8 presents a process arrangement similar to FIG. 7 with the addition of a gas water vapor separator on the gas stripping units' (E) effluent gas stream. Ammonia stripping is improved at higher temperatures. But, the higher temperatures also strip larger quantities of water vapor that remove heat from the process and dilute the reclaimed ammonia concentration. To reduce heat losses in the stripping unit and produce a more concentrated product, removal and recycle of water vapor is desired. FIG. 8 shows a water vapor-permeable membrane (M) on the stripping gas effluent line that withdraws and recycles warm water vapor to the gas stripping unit by use of a vacuum blower (Blower). FIG. 10 presents an example of such a membrane arrangement.

FIG. 9 presents an alternative arrangement of FIGS. 7 and 8 wherein the process effluent is used to remove carbon dioxide from a $CO_2$ rich gas to produce a $CO_2$ lean gas that is used to produce a $CO_2$-deficient gas through the ammonia recovery process shown in FIG. 5. In many cases the production of a $CO_2$-deficient gas, such as biomethane (natural gas), is predicated on having a sufficient quantity of ammonia to remove the large quantity of $CO_2$. In most cases $NH_3$ availability is limiting. Supplemental ammonia can be acquired to consume the excess $CO_2$, at a cost. Or, a portion of the excess $CO_2$ can be removed through a carbonation unit, shown in FIG. 9. The FIG. 9 configuration uses the high pH, high alkalinity liquid effluent to remove $CO_2$ from the $CO_2$-rich gas and thereby produce a more acceptable, lower pH liquid effluent.

FIG. 10 presents one of many possible configurations for the removal of warm water vapor from the stripped ammonia gas. Suitable materials such as silicone gas permeable membranes have water vapor permeabilities six to ten times the permeability of ammonia gas. The example shown in FIG. 10 presents a typical packed stripping tower with influent and effluent water streams as well as influent and effluent gas streams. The stripped gas leaving the stripping tower (Gas Out) contains the ammonia gas and water vapor. The gas and water vapor is passed through a series of membranes where a differential pressure is applied (gas out p+ vacuum p). The water vapor-enriched gas will pass through the membrane at a higher rate than the ammonia-enriched retentate that will be processed through the downstream condenser (FIG. 4). The warm, water vapor-enriched gas is then conveyed through the inlet recirculating gas blower and reprocessed through the stripping tower. In the alternative, an eductor can be used instead of, or in conjunction with, a vacuum pump.

I claim:

1. A method for recovering ammonia from a process of anaerobic digestion, comprising the steps of:
    (a) anaerobically digesting an organic, nitrogen containing substrate to produce a turbid digested liquid containing ammonia, carbon dioxide, methane and suspended solids;
    (b) introducing the digested liquid of step (a) to a culture of phototrophic microorganisms capable of consuming $CO_2$ and bicarbonate in the presence of natural or artificial light, the culture having a surface to volume ratio sufficiently high that light transmission to the culture is adequate for the culture to uptake carbon dioxide and bicarbonate from the digested liquid of step (a) and accumulate biomass, thereby producing a liquid media having an elevated pH;
    (c) stripping ammonia gas from the liquid media produced in step (b) with a stripping gas that does not include biogas or methane, thereby producing a mixture of water vapor, stripping gas and stripped ammonia gas stream and an ammonia-deficient liquid stream; and
    (d) condensing the mixture of water vapor, stripping gas and stripped ammonia gas stream in a condenser to form a liquid ammonia condensate, water and cooled stripping gas.

2. The method of claim 1, wherein the liquid media produced in step (b) is heated to 30° to 80° C. prior to step (c).

3. The method of claim 2, wherein the heating of the liquid media produced in step (b) occurs in the same vessel as step (b).

4. The method of claim 1, further comprising anaerobically digesting the biomass accumulated from the growth of microorganisms in step (b) to produce biogas.

5. The method of claim 1, wherein, step (b) and step (c) occur in the same vessel.

6. The method of claim 1, further comprising restripping the liquid ammonia condensate formed in step (d) to form a more concentrated liquid ammonia condensate.

7. The method of claim 1, wherein the condensate formed in step (d) is subsequently used to precipitate ammonium bicarbonate from a carbon dioxide-enriched gas in the presence of water.

8. The method of claim 1, further comprising, pretreating the digested liquid from step (a) to remove suspended solids prior to step (b).

9. The method of claim 1, further comprising pretreating the digested liquid from step (a) to remove $CO_2$ prior to step (b).

10. The method of claim 1, wherein said culture of phototrophic microorganisms capable of consuming $CO_2$ and bicarbonate is grown in a rotating photobioreactor, which comprises:
    illumination by artificial or natural light;
    a substantially enclosed vessel containing media and is capable of exposing the media to light; and within the vessel is a shaft aligned along a shaft axis for rotation about the axis;
    a plurality of axially spaced-apart, growth plates attached to the shaft, and rotatable with the shaft about the axis; and
    wherein the speed of rotation of the shaft can be varied.

11. The method of claim 10, wherein the photobioreactor is capable of varying the intensity of the natural or artificial light.

12. The method of claim 11, wherein the rotational speed and the intensity of the natural or artificial light are set such that the pH of the culture of phototrophic microorganisms capable of consuming $CO_2$ and bicarbonate is maintained within the range of 8.3 to 11.0.

13. The method of claim 1, wherein in step (c) the stripping gas is applied within a gas stripping unit which strips ammonia from the liquid media produced in step (b), thereby producing an ammonia-deficient liquid stream and a mixture of water vapor, stripping gas and stripped ammonia gas stream.

14. The method of claim 13, further comprising heating the cooled stripping gas from step (d) and reintroducing this reheated stripping gas back into said gas stripping unit to recover any residual ammonia and water vapor.

15. The method of claim 13, further comprising cooling the mixture of water vapor, stripping gas and stripped ammonia gas stream produced in step (c) prior to condensing in step (d).

16. The method of claim 15, further comprising using a heat exchanger to heat the cooled stripping gas from step (d) and reintroducing this reheated stripping gas back into the gas stripping unit to recover any residual ammonia and water vapor.

17. The method of claim 7, wherein the ammonium bicarbonate is precipitated in the form of pellets.

18. The method of claim 17, further comprising coating said pellets with a polymer-like substance.

19. The method of claim 1, wherein carbon dioxide produced during said anaerobic digestion of liquid waste in step (a) is combined with stripped ammonia condensate in step (d).

20. The method of claim 1, wherein the stripped liquid media produced in step (c) is recycled into the liquid culture of step (b).

21. The method of claim 2, further comprising using a heat pump to apply waste heat from the condensing of step (d) to heat the liquid media and to cool the mixture of water vapor, stripping gas and stripped ammonia gas produced in step (c).

22. The method of claim 1, further comprising the additional step of:
(c') passing a portion of the gas mixture produced in step (c) through a gas-permeable membrane prior to cooling the same, thereby removing water vapor and latent heat from the gas mixture and producing a water vapor-enriched recycle stream that is added to step (c) and an ammonia-enriched retentate to be cooled and condensed,
wherein the remaining portion of the gas mixture, if any, continues to step (d).

23. The method of claim 22, wherein in step (c) the stripping of the ammonia gas occurs within a gas stripping unit and the water vapor-enriched recycle stream from step (c') is added to this gas stripping unit.

24. A method for recovering ammonia from a process of anaerobic digestion, comprising the steps of:
(a) anaerobically digesting an organic, nitrogen containing substrate into a turbid, digested liquid containing ammonia, carbon dioxide, methane and suspended solids;
(b) blending the liquid from step (a) with a liquid having elevated pH, thereby producing a blended, liquid effluent;
(c) stripping ammonia gas from the blended, liquid effluent produced in step (b) within a gas stripping unit with a stripping gas that does not include biogas or methane, thereby producing an ammonia-deficient liquid stream and an ammonia and water vapor-enriched gas stream combined with the stripping gas; and
(d) introducing at least a portion of the ammonia-deficient liquid stream produced in step (c) to a culture of phototrophic microorganisms capable of consuming $CO_2$ and bicarbonate in the presence of natural or artificial light, the culture having a surface to volume ratio sufficiently high that light transmission to the culture is adequate for the culture to uptake carbon dioxide and bicarbonate from the ammonia-deficient liquid stream, accumulate biomass, and produce a liquid media having an elevated pH;
(e) cooling the ammonia and water vapor-enriched gas stream combined with the stripping gas produced in step (c);
(f) condensing the ammonia and water vapor-enriched gas stream combined with the stripping gas from step (e) in a condenser to form a liquid ammonia condensate and a cooled stripping gas; and
(g) heating the cooled stripping gas containing any remaining, unreacted, ammonia and water vapor in step (f) and reintroducing this heated stripping gas back into said gas stripping unit in step (c); and
(h) using the liquid media produced in step (d) as the liquid having elevated pH in step (b).

25. The method of claim 24, further comprising introducing a purge gas to said culture of phototrophic microorganisms capable of consuming $CO_2$ and bicarbonate in step (d).

26. The method of claim 24, further comprising passing the digested liquid of step (a) through a liquid/solids separator prior to step (b) and passing a purge gas through the liquid/solids separator, thereby producing a carbon dioxide-enriched gaseous effluent from said liquid/solids separator.

27. The method of claim 24, further comprising anaerobically digesting the biomass accumulated in step (d) to produce biogas.

28. The method of claim 24, further comprising stripping carbon dioxide from the digested liquid produced in step (a).

29. The method of claim 24, wherein suspended solids are removed from the digested liquid in step (a) and carbon dioxide is stripped from the digested liquid produced in step (a) by a vacuum flotation degassing unit prior to step (b).

30. The method of claim 24, wherein the stripping gas is air.

31. The method of claim 24, wherein said culture of phototrophic microorganisms capable of consuming $CO_2$ and bicarbonate is grown in a rotating photobioreactor, which comprises:
illumination by artificial or natural light;
a substantially enclosed vessel that is capable of exposing the media to light; and within the vessel a shaft aligned along a shaft axis for rotation about the axis;
a plurality of axially spaced-apart, growth plates attached to the shaft, and rotatable with the shaft about the axis; and
wherein the speed of rotation can be varied.

32. The method of claim 31, wherein the photobioreactor is capable of varying the intensity of the natural or artificial light.

33. The method of claim 32, wherein the rotational speed and the intensity of the natural or artificial light are set such that the pH of the culture of phototrophic microorganisms capable of consuming $CO_2$ and bicarbonate is maintained within the range of 8.3 to 11.

34. The method of claim 24, further comprising the additional step of:
(d') passing a portion of the water vapor-enriched gas stream combined with the stripping gas produced in step (c) through a gas-permeable membrane prior to cooling the same, thereby removing water vapor and latent heat from the gas stream and producing a water vapor enriched recycle stream that is added to step (e) and an ammonia-enriched retentate to be cooled and condensed
wherein the remaining portion of the ammonia and water vapor-rich gas stream combined with the stripping gas continues to step (d).

35. The method of claim 34, further comprising adding a portion of the water vapor-enriched recycle stream back to the gas stripping unit of step (c).

36. The method of claim 24, further comprising adding a portion of the ammonia-deficient liquid produced in step (c) to the blended, liquid effluent formed in step (b).

37. The method of claim 36, further comprising adding carbon dioxide from a carbon dioxide source to the ammonia-deficient liquid produced in step (c), thereby decreasing the pH of the ammonia-deficient liquid.

38. The method of claim 37, wherein said carbon dioxide source is biogas.

39. The method of any of claims 24-38, wherein step (c) and step (d) occur in the same vessel.

40. The method of any of claims 24-38, further comprising restripping the liquid ammonia condensate formed in step (f) to form a more concentrated liquid ammonia condensate.

41. The method of any of claims 24-38, wherein the liquid ammonia condensate formed in step (f) is subsequently used to precipitate ammonium bicarbonate from a carbon dioxide-rich gas in the presence of water.

* * * * *